United States Patent [19]
Johnson

[11] 3,932,270
[45] Jan. 13, 1976

[54] METHOD FOR DETERMINING HYDROCARBON HYDROTREATING ACTIVITY OF A CATALYST PRIOR TO ITS USE IN A HYDROTREATING PROCESS

[75] Inventor: Marvin F. L. Johnson, Homewood, Ill.

[73] Assignee: Atlantic Richfield Company, Philadelphia, Pa.

[22] Filed: Feb. 20, 1975

[21] Appl. No.: 551,563

Related U.S. Application Data

[62] Division of Ser. No. 470,885, May 17, 1974.

[52] U.S. Cl. .............................................. 208/216
[51] Int. Cl.² ....................................... C10G 23/02
[58] Field of Search ................ 208/216, 217, 254 H

[56] References Cited
UNITED STATES PATENTS 3,682,836  8/1972  Jaffe ................................. 208/216
3,749,664  7/1973  Mickelson ....................... 208/254 H Primary Examiner—Delbert E. Gantz
Assistant Examiner—G. J. Crasanakis
Attorney, Agent, or Firm—Frank J. Uxa

[57] ABSTRACT

An improved method of hydrocarbon hydrotreating is disclosed wherein the activity of a hydrotreating catalyst is determined prior to the catalyst being used to promote hydrocarbon hydrotreating. The catalytic activity of such a catalyst is determined by comparing a parameter involving the relative reflectance of the catalyst relative to the relative reflectance of a standard catalyst having acceptable activity. When it is determined that a given catalyst has catalytic activity at least essentially equal to that of the standard catalyst, the catalyst may be used to promote hydrocarbon hydrotreating thus providing an improved method of hydrocarbon hydrotreating.

7 Claims, No Drawings

METHOD FOR DETERMINING HYDROCARBON HYDROTREATING ACTIVITY OF A CATALYST PRIOR TO ITS USE IN A HYDROTREATING PROCESS

This is a division of application Ser. No. 470,885, filed May 17, 1974.

The present invention relates to an improved method of hydrocarbon hydrotreating. More particularly, the present invention relates to an improved method of hydrocarbon hydrotreating wherein the hydrocarbon hydrotreating activity of a catalyst is determined prior to the catalyst being used to promote hydrocarbon hydrotreating.

Various hydrocarbonaceous materials may contain minor amounts of contaminants such as sulfur, nitrogen and the like. One effective method of reducing the concentration of these contaminants in such hydrocarbon is hydrocarbon hydrotreating. Such hydrotreating often involves contacting the contaminated hydrocarbon with hydrogen in the presence of a catalyst effective to promote the hydrotreating, e.g., hydrodesulfurization, hydrodenitrogenation and the like, of the hydrocarbon.

Much work has been done to obtain good hydrocarbon hydrotreating catalysts. Catalysts which comprise a major amount of a solid porous support, and minor, catalytically effective amounts of nickel and at least one metal selected from the group consisting of molybdenum, tungsten and mixture thereof are known to be particularly effective hydrocarbon hydrotreating catalysts.

However, even with the catalysts as described above, certain processing disadvantages have been apparent. For example, after a period of time in hydrocarbon hydrotreating service, these catalysts become deactivated and/or cannot be used because of a build-up of carbonaceous deposits on the catalysts. The catalysts are often subjected to high temperature oxidation to remove these deposits and regenerate, e.g., restore the catalytic activity of the catalyst. In certain instances, such oxidative treatment, although substantially removing the deposits from the catalyst, has resulted in a catalyst having unacceptable hydrocarbon hydrotreating activity. Also, in certain instances virgin catalysts of the type described above have been found to have unacceptable hydrocarbon hydrotreating activity. Processing with a catalyst having unacceptable activity is highly undesirable, for example, because of hydrotreating reaction inefficiency as well as possible detrimental effects to processing using the product of such a hydrotreating operation. Thus, it would be advantageous to determine the hydrocarbon hydrotreating activity of a catalyst prior to its being used to promote such hydrotreating.

Therefore, one of the objects of the present invention is to provide an improved method for determining the hydrocarbon hydrotreating activity of a catalyst prior to using the catalyst to promote hydrocarbon hydrotreating.

Another object of the present invention is to provide an improved method of hydrocarbon hydrotreating in which the activity of a catalyst is determined prior to using the catalyst to promote hydrocarbon hydrotreating. Other objects and advantages of the present invention will become apparent hereinafter.

A method has now been discovered for determining the hydrocarbon hydrotreating, e.g., hydrodesulfurization, activity of a first catalyst prior to the catalyst being used to promote hydrocarbon hydrotreating, e.g., hydrodesulfurization. The first catalyst comprises a major amount of a solid porous support, e.g., alumina, a minor, catalytically-effective amount of nickel at least a portion of which is present in the first catalyst in the Ni++ form and a minor, catalytically-effective amount of at least one metal selected from the group consisting of molybdenum, tungsten and mixtures thereof, at least a portion of the metal being present in an oxidized state. The present method comprises:

1. determining the maximum relative reflectance of the first catalyst of light having a wave number in the range from about 16,000 cm.$^{-1}$ to about 1700 cm.$^{-1}$;
2. determining the maximum relative reflectance of the first catalyst of light having a wave number of about 20,000 cm.$^{-1}$;
3. determining an activity ratio equal to the relative reflectance determined in step (1) minus the relative reflectance determined in step (2);
4. performing steps (1), (2) and (3) to determine the activity ratio of a standard catalyst having essentially the same elemental composition as the first catalyst and having acceptable hydrocarbon hydrodesulfurization activity; and
5. comparing the activity ratio obtained in steps (3) and (4), provided that (a) an increase in activity ratio from step (3) to step (4) being indicative of reduced hydrocarbon hydrotreating activity of the first catalyst relative to the standard catalyst, (b) no change in activity ratio from step (3) to step (4) being indicative of essentially equal hydrocarbon hydrotreating activity of the first catalyst relative to the standard catalyst, and (c) a decrease in activity ratio from step (3) to step (4) being indicative of greater hydrocarbon hydrotreating activity of the first catalyst relative to the standard catalyst.

An improved hydrocarbon hydrotreating process has also been discovered which comprises (1) determining the hydrocarbon hydrotreating activity of a first catalyst in the manner described above; (2) contacting a hydrocarbon feedstock containing at least one contaminant selected from the group consisting of sulfur, nitrogen and mixtures thereof with hydrogen in the presence of a first catalyst at conditions such that hydrogen forms compounds with at least one of the contaminants, provided that the first catalyst has a hydrocarbon hydrotreating activity at least essentially equal to the activity of the standard catalyst; and (3) recovering a hydrocarbon material having a reduced content of at least one of the contaminants relative to the feedstock.

In many instances, only a minor portion, e.g., a sample, of a mass of first catalyst is used to determine the hydrocarbon hydrotreating activity of the first catalyst. If it is determined that this activity is at least essentially equal to the activity of the standard catalyst, the remaining mass of the first catalyst, with or without the portion used to determine the activity of this catalyst, may be used in the hydrocarbon hydrotreating process described above.

The term "relative reflectance" as used herein is defined as:
$$\log(Ro/R)$$
wherein Ro is the percent reflectance of a reference material at a specified wave number and R is the percent reflectance of the catalyst sample, e.g., first catalyst and standard catalyst, at that wave number.

Suitable reference materials include substances which reflect at least about 80 percent, preferably at least about 95 percent, of the light of a specified wave number. Specific examples of such reference materials include magnesium oxide, magnesium carbonate, magnesium sulfate, barium sulfate, lithium carbonate, sodium chloride, sodium fluoride, alumina, silica gel and the like. The preferred reference material for use in the present invention is magnesium oxide.

The statement that the standard catalyst has essentially the same elemental composition as the first catalyst means that the standard catalyst comprises a major amount of a solid porous support, a minor, catalytically-effective amount of nickel at least a portion of which is present in the N++ form, and minor, catalytically-effective amount of the other metal or metals, at least a portion of which being present as metal oxide, which comprise the first catalyst. Preferably, the standard catalyst has substantially the same porous solid support as the first catalyst and has substantially the same relative proportions of elements as the first catalyst.

The catalyst suitable for the present method include a solid porous support, e.g., alumina. It is preferred that the solid porous support be a material comprising a major amount of alumina having a surface area of from about 25 m.$^2$/gm. to about 500 m.$^2$/gm. The solid porous support comprises a major proportion, preferably at least about 60 percent, and more preferably at least about 65 percent, by weight of the catalyst. One specific catalyst support, or base, is alumina derived from hydrous alumina, preferably, predominating in a material selected from the group consisting of alumina trihydrate, alumina monohydrate, amorphous hydrous alumina and mixtures thereof, more preferably from the group consisting of alumina monohydrate, amorphous hydrous alumina and mixtures thereof, which alumina when formed as pellets and calcined, has an apparent bulk density of from about 0.35 gm./cc. to about 1.00 gm./cc., pore volume from about 0.45 ml./gm. to about 1.50 ml./gm., and surface area from about 100 m.$^2$/gm. to about 500 m.$^2$/gm. The solid porous support may contain, in addition, minor proportions of other well known refractory inorganic oxides such as silica, zirconia, magnesia and the like.

The alumina support may be synthetically prepared in any suitable manner. Thus, for instance, hydrated alumina in the form of a hydrogel can be precipitated from an aqueous solution of a soluble aluminum salt such as aluminum chloride. Ammonium hydroxide is a useful agent for effecting the precipitation. Control of the pH to maintain it within the values of about 7 to about 10 during the precipitation is desirable for obtaining a good rate of conversion. Extraneous ions, such as halide ions, which are introduced in preparing the hydrogel, can, if desired, be removed by filtering the alumina hydrogel from its mother liquor and washing the filter cake with water. Also, if desired, the hydrogel can be aged, say for a period of several days. The effect of such aging is to build up the concentration of alumina trihydrate in the hydrogel.

The first catalyst, the activity of which may be determined using the method of the present invention preferably comprises at least one component, i.e., a minor amount of phosphorus, sufficient to improve the hydrocarbon hydrotreating activity of the catalyst in addition to the metallic component described above. Preferably, the phosphorus content of these catalysts is within the range from about 0.5 to about 15 percent, more preferably from about 1 to about 10 percent, of the total catalyst. One preferred method by which phosphorus may be included in these catalysts comprises contacting an aqueous mixture of hydrous alumina with at least one phosphorus-containing compound including at least one acidic hydrogen atom, i.e., phosphorus acids, in an amount sufficient to increase the hydrocarbon hydrotreating activity of the final catalyst and forming a phosphorus-containing hydrous alumina. The aqueous mixture preferably comprises from about 5 to about 70 percent, more preferably from about 30 to about 70 percent, by weight of hydrous alumina (calculated as $Al_2O_3$). The hydrous alumina used may be prepared by various methods known in the art, as noted previously. It is not critical in what order the components are combined in this contacting step. For example, water containing the phosphorus acid can be combined with dried hydrous alumina; the phosphorus acid or a concentrated mixture of water and phosphorus acid can be combined with an aqueous mixture of hydrous alumina; or the phosphorus acid, water and hydrous alumina from separate sources can be combined for the contacting step. The contacting step may occur in a batch system, semi-batch system or a continuous system.

This contacting takes place under conditions sufficient to increase the hydrocarbon hydrotreating activity of the first catalyst. Although the contacting conditions are not critical, it is preferred that the contacting take place at a temperature in the range from about 35°F. to about 210°F., or more, more preferably in the range from about 50°F. to about 150°F. Contacting times in the range from about 1 minute or less to about 20 hours or more may be used, with times in the range from about 1 minute to about 1 hour being preferred. The contacting step preferably takes place at conditions, e.g., temperatures and pressures, such that a substantial loss, e.g., greater than 30%, of the free water in the aqueous mixture by vaporization is avoided. Thus, for example, the contacting of step (1) may be carried out at pressures in the range from about 1 atmosphere to about 10 atmospheres or more.

The phosphorus acids referred to above are chosen to provide a first catalyst having increased hydrocarbon hydrotreating activity. Preferably, the phosphorus acid is at least partially water soluble. Also included in the term phosphorus acids are phosphorus acid precursors, that is phosphorus-containing compounds able to form compounds containing at least one acidic hydrogen atom when in the presence of water such as phosphorus oxides, phosphorus oxyhalides and the like. Included among the phosphorus acids useful in the present invention are ortho-, pyro-, meta-, hypo-phosphorus acids, phosphoric acids, phosphonic acids, phosphinic acids, phosphenic acids, phosphoranoic acids, phosphoranedioic acids, phosphoranetrioic acids, phosphorcientetroic acids, phosphoranepentoic acids and mixtures thereof. Preferably, the phosphorus acid used is selected from the group consisting of phosphoric acids, phosphorous acids and mixtures thereof. Of course, mixtures of two or more phosphorus acids may be utilized. Substituted forms of the phosphorus acids also may be used. Suitable substituents are chosen so as not to materially interfere with the functions of the phosphorus acids. Such substituents include: halide, such as fluoride, chloride, bromide and the like; $NH_4$; CN; monovalent essentially hydrocarbonaceous radicals containing from about 1 to about 30 or more carbon atoms and the like. Among the monovalent essentially hydrocarbonaceous radicals which may be substituted on to phosphorus acids are alkyl and alkenyl such as methyl, ethenyl, butyl, butenyl, octyl, octenyl, hexyldecyl, hexyldecenyl and the like; aryl such as phenyl, naphthyl and the like; and alkaryl, alkenaryl, aralkyl and aralkenyl such as methyl-, butyl- and decyl-phenyl, ethenyl- butenyl- and decenyl-phenyl, benzyl, phenyl butyl, phenyl decyl, phenyl ethenyl, phenyl butenyl, phenyl decenyl and the like. Substituted monovalent hydrocarbonaceous radicals may be used, for example, to improve water solubility of the acid, provided that the substituent does not interfere with the functions of the phosphorus acids.

In a more preferred embodiment, the phosphorus acid used in selected from the group consisting of phosphoric acids and mixtures thereof. The term phosphoric acids includes compounds which form phosphoric acids in the presence of water. It is preferred that the phosphorus acid be present in the contacting step in an amount such that at least about 0.01 moles, more preferably from about 0.01 mole to about 2.0 moles, most preferably from about 0.05 mole to about 1.0 moles, of phosphorus is present per mole of alumina (calculated as $Al_2O_3$).

This contacting step forms a phosphorus-containing hydrous alumina which can, if necessary, be dried. In any event, the alumina, whether phosphorus-containing or not, may be formed into macrosize particles of any desired shape such as pills, cakes, extrudates, powders, granules, spheres, and the like using conventional methods. The size selected for the macrosize particles can be dependent upon the intended environment in which the final catalyst is to be used — as, for example, whether in a fixed or moving bed reaction system. Thus, for example, whereas in the preferred embodiment of the present invention, the final catalyst is designed for use in hydrocarbon hydrotreating operations employing a fixed bed of catalyst, the alumina will preferably be formed into particles having a minimum dimension of at least about 0.01 inch and a maximum dimension up to about one-half inch or one inch or more. Spherical particles having a diameter of about 0.03 inch to about 0.25 inch., preferably about 0.03 inch to about 0.15 inch, are often useful.

It is essential that the catalysts suitable for the method of the present invention contain a minor catalytically-effective amount of nickel at least a portion, preferably substantially all, of which is present in the N++ form. The nickel component preferably comprises from about 0.5 to about 15 percent, more preferably from about 1.5 to about 7 percent, by weight of the total catalyst (calculated as elemental nickel).

These catalysts also contain a minor, catalytically-effective amount of at least one other metal selected from the group consisting of molybdenum, tungsten and mixtures thereof, provided that at least a portion, preferably substantially all, of the metal is present in the catalyst in an oxidized state. The additional catalyst metal component or components preferably comprise a total from about 5 to about 40 percent, more preferably from about 10 to about 30 percent by weight of the total catalyst (calculated as the tri-oxide).

Although any conventional method may be used to produce the N++ containing catalysts suitable for the present invention, a convenient means involves the use of impregnating techniques on a preformed porous solid support, for example, comprising a major portion of alumina. For example, the catalyst may be prepared by contacting the solid porous support, e.g., in the form of particles of any suitable size and shape, with a single aqueous impregnating solution of suitable water-soluble compounds of nickel, e.g., nickel nitrate, formate, sulfate, chloride and the like, and water-soluble compounds of at least one additional metallic component, e.g., ammonium molybdate, ammonium tungstate and the like. To illustrate, an aqueous solution of nickel nitrate and ammonium molybdate in ammonia and water can be used as the impregnating solution. Alternatively, ammonium molybdate can be dissolved in a solution of aqueous ammonia, nickel nitrate is then added to this solution to form the nickel amine complex ($Ni(NH_3)_6$++). This solution can then be used to impregnate the support. A double impregnation technique may be used whereby the additional metallic component is incorporated into this porous solid support, by, for example, contacting the porous solid support with an aqueous impregnating solution of a water soluble compound of the additional metallic component. The thus impregnated porous solid support may be dried and subjected to high temperature calcination. In any event, the porous solid support containing the additional metallic component is then contacted with an aqueous solution of a suitable water-soluble compound of nickel to form a solid product comprising nickel in the required N++ form. The order in which the metals are incorporated into the porous solid support is not critical. Thus, the nickel may be incorporated into the porous solid support prior to an additional metallic component, as well as vice versa.

In any event, the metal-containing solid porous support is subjected to high temperature calcination in an oxygen-containing atmosphere in order, for example, to improve the general toughness and attrition resistance of the catalyst as well as providing optional catalytic properties prior to it being used in hydrocarbon hydrodesulfurization service. It is at this point, i.e., after calcination, that the present method for monitoring catalyst activity is preferably carried out.

In another preferred embodiment, the present method is carried out on a first catalyst after it has been used to promote hydrocarbon hydrotreating for a period of time and has been subjected to regeneration procedures, e.g., contact with an oxygen-containing atmosphere to remove the carbonaceous deposits formed on the catalyst during the hydrotreating operation.

If, using the method of the present invention, it is determined that the activity of the first catalyst is at least equal to the activity of the standard catalyst, such first catalyst may be used to provide an improved hydrocarbon hydrotreating process. These first catalysts are particularly useful in the hydrotreating of substantially hydrocarbon feedstocks such as sulfur-containing and/or nitrogen-containing mineral oil derived from petroleum, coal, shale oil, tar sand oil and the like. Distillate feedstocks, including heavy oil distillates, having end boiling point up to about 1100°F., are especially preferred. Typical distillates which may be processed using the present catalyst include those having at least about 0.5 percent by weight sulfur and/or at least about 100 ppm. nitrogen and boiling primarily in the range from about 150°F. to about 1050°F., or more. The substantially hydrocarbon feedstock can be contacted with hydrogen in the presence of the first catalyst the activity of which has been determined to be at least equal to the activity of a standard catalyst in at least one reaction zone at conditions such as a temperature, for example, in the range from about 650°F. to about 900°F., preferably from about 700°F. to about 850°F., sufficient to form compounds of at least one of the contaminants of the feedstock, e.g., sulfur and/or nitrogen, with hydrogen which can be removed by conventional processing, e.g., flashing, simple distillation, vacuum distillation and the like. Other suitable contacting conditions include pressures from about 300 psi. to about 5000 psi., preferably from about 300 psi. to about 1500 psi.; weight hourly space velocities of from about 0.5 to about 4, preferably from about 1 to about 3 and hydrogen flow rates of from about 300 to about 30,000 standard cubic feet of hydrogen per barrel of feedstock, preferably from about 300 to about 5,000 standard cubic feet of hydrogen per barrel of feedstock. In many instances, contact of the feedstock over the catalyst as set forth above allows the recovery of at least one substantially hydrocarbon product having a sulfur concentration and/or nitrogen concentration reduced from that of the feedstock. This product recovery can be carried out using conventional techniques, e.g., flashing, distillation and the like, well known in the art.

The following examples illustrate clearly the present invention. However, these examples are not to be interpreted as specific limitations on the invention.

EXAMPLES 1 to 5

Five samples of commercially available hydrocarbon hydrotreating catalyst were chosen for testing. Each of the catalysts were prepared using conventional techniques. These samples of alumina-supported catalyst had the following properties.

|  | SAMPLE NOS. | | | | |
| --- | --- | --- | --- | --- | --- |
|  | 1 | 2 | 3 | 4 | 5 |
| Nickel Content, [1] Wt.% | 2.09 | 2.52 | 3.05 | 2.75 | 2.7 |
| Molybdenum Content, [2] Wt.% | 14.25 | 16.37 | 13.29 | 15.86 | 14.8 |
| Phosphorus Content, Wt. | 1.21 | 0.93 | 1.26 | 0.74 | 0.9 |
| Silica Content, Wt.% | — | 1.45 | 1.45 | 1.58 | 1.4 |
| Surface Area, m²./gm. | 231 | 248 | 240 | 263 | 26 |
| Total Pore Volume, cc./gm. | 0.516 | 0.600 | 0.569 | 0.609 | 0.58 |

[1] The nickel content is calculated as elemental nickel and is present in the Ni++ form.
[2] The molybdenum content is calculated as $MoO_3$.

Each of these catalysts samples was subjected to testing using a Cary U-V spectrophotometer provided with a reflectance attachment to determine the reflectance of light having a wave number of 16,000 cm.$^{-1}$ and light having a wave number of 20,000 cm.$^{-1}$. The reflectance of light by the sample was compared to the reflectance of light of a given wave number of a standard material, in this instance magnesium oxide. The relative reflectance of each catalyst sample of light having wave numbers of 16,000 cm.$^{-1}$ and 20,000 cm.$^{-1}$ was determined. An activity ratio, defined as (Relative Reflectance) 16,000 cm.$^{-1}$ minus (Relative Reflectance) 20,000 cm.$^{-1}$ was determined for each catalyst sample. A compilation of these activity ratios is as follows:

| Catalyst Sample No. | Activity Ratio* |
| --- | --- |
| 1 | −0.05 |
| 2 | +.003 |
| 3 | +0.012 |
| 4 | +0.038 |
| 5 | +0.103 |

*The Activity Ratios of both catalyst Samples 1 and 2 are averages of determinations made on two portions of the catalyst.

Samples of each catalyst were tested in hydrocarbon, e.g., light cycle oil, hydrotreating service to determine the hydrodesulfurization activity of the particular catalyst. Typical reaction conditions for this testing are as follows:

| | |
| --- | --- |
| Temperature, °F. | 650 to 725 |
| Pressure, psig. | 400 to 2000 |
| WHSV | 0.5 to 6.0 |
| $H_2$/Hydrocarbon | 2000 to 3000 |
| Sulfur Content of Hydrocarbon Feedstock, Wt.% | 0.9 to 1.3 |

Using correlation techniques known to be reasonably accurate, the results, e.g., degree of desulfurization and reaction severity, from each test were compared to the results predicted by these correlation techniques. The ratio of $$\frac{\text{Predicted Reaction Severity*}}{\text{Actual Reaction Severity*}}$$

*Reaction Severity to achieve the same degree of desulfurization.

was defined as the Relative Activity of the catalyst sample. The greater the Relative Activity the more active the catalyst for hydrocarbon desulfurization. The Activity Ratios and Relative Activities of the catalyst samples were found to be as follows:

| Catalyst Sample No. | Activity Ratio | Relative Activity |
| --- | --- | --- |
| 1 | −0.05 | 1.25 |
| 2 | +0.003 | 1.07 |
| 3 | +0.012 | 1.02 |
| 4 | +0.038 | 0.98 |
| 5 | +0.103 | 0.91 |

The above tabulations show quite clearly that the method of the present invention provides a convenient method for determining the hydrotreating, e.g., hydrodesulfurization, activity of various catalysts. For example, it can be seen that as the Activity Ratio is increased, the Relative Activity of the catalyst is decreased. If Catalyst 3 is defined as a standard catalyst having minimum acceptable hydrocarbon hydrotreating activity, it can be seen that Catalysts 4 and 5 which have higher Activity Ratio than does Catalyst 3, have unacceptable hydrocarbon hydrotreating catalytic activity. Conversely, catalyst sample numbers 1 and 2 which have Activity Ratios less than Catalyst 3 have greater hydrotreating activity than does Catalyst 3.

EXAMPLES 6 and 7

The catalysts of Example 1 and 2 above, having been shown to have acceptable hydrocarbon hydrotreating activity, are utilized in hydrocarbon hydrotreating service. The hydrocarbon to be treated is a petroleum derived distillate containing sulfur as a contaminant. This hydrocarbon is contacted with each of the catalysts in the presence of hydrogen at conditions such that hydrogen forms compounds with the sulfur. The catalysts of Examples 1 and 2 both exhibit said hydrotreating catalytic activity. After such contacting, a hydrocarbon product having reduced sulfur content relative to the hydrocarbon feedstock is recovered using conventional means.

While this invention has been described with respect to various specific examples and embodiments, it is to be understood that the invention is not limited thereto and that it can be variously practiced within the scope of the following claims.

The embodiments of the invention in which an exclusive property or privelege is claimed are defined as follows:

1. A hydrocarbon hydrotreating process which comprises:
  1. determining the hydrocarbon hydrotreating activity of a first catalyst comprising a major amount of a porous alumina support, a minor catalytically-effective amount of nickel, at least a portion of said nickel being present in the Ni++ form, and a minor catalytically-effective amount of at least one additional metal selected from the group consisting of molybdenum, tungsten, and mixtures thereof, at least a portion of said one additional metal being presesnt in an oxidized state, said hydrocarbon hydrotreating activity being determined according to a method comprising:
     a. determining the maximum relative reflectance of said first catalyst of light having a wave number in the range from about 16,000 cm.$^{-1}$ to about 17,000 cm.$^{-1}$;
     b. determining the maximum relative reflectance of said first catalyst of light having a wave number of about 20,000 cm$^{-1}$;
     c. determining an activity ratio equal to the relative reflectance determined in step (a) minus the relative reflectance determined in step (b);
     d. performing steps (a), (b) and (c) to determine the activity ratio of a standard catalyst having essentially the same elemental composition as said first catalyst and acceptable hydrocarbon hydrotreating activity;
     e. comparing the activity ratios obtained in steps (c) and (d), provided that (1) an increase in activity ratio from step (c) to step (d) being indicative of reduced hydrocarbon hydrotreating activity of said first catalyst relative to said standard catalyst, (2) no change in activity ratio from step (c) to step (d) being indicative of essentially equal hydrocarbon hydrotreating activity of said first catalyst relative to said standard catalyst and (3) a decrease in activity ratio from step (c) to step (d) being indicative of greater hydrocarbon hydrotreating activity of said first catalyst relative to said standard catalyst;
  2. contacting a hydrocarbon feedstock containing at least one contaminant selected from the group consisting of sulfur, nitrogen and mixtures thereof with hydrogen in the presence of said first catalyst at conditions such that hydrogen forms compounds with at least one of said contaminants, provided that said first catalyst has a hydrocarbon hydrotreating activity at least essentially equal to that of said standard catalyst; and
  3. recovering a hydrocarbon material having a reduced content of at least one of said contaminants relative to said feedstock.

2. The method of claim 1 wherein substantially all of the nickel of said first catalyst is in the Ni++ form.

3. The method of claim 2 wherein said standard catalyst has substantially the same relative proportions of elements as said first catalyst.

4. The method of claim 3 wherein said nickel is present in said first catalyst in an amount of from about 0.5 to about 15 percent by weight of said first catalyst.

5. The method of claim 4 wherein said additional metal is present in said first catalyst in an amount from about 5 to about 40 percent by weight of said first catalyst (calculated as the metal trioxide).

6. The method of claim 5 wherein said first catalyst further includes a minor amount of phosphorus sufficient to improve the hydrocarbon hydrotreating activity of said first catalyst.

7. The method of claim 6 wherein said nickel is present in said first catalyst in an amount of from about 1.5 to about 7 percent by weight of said first catalyst.

* * * * *